United States Patent [19]

Howland

[11] 4,257,690

[45] Mar. 24, 1981

[54] EYE TESTING CHART

[75] Inventor: Bradford Howland, Cambridge, Mass.

[73] Assignee: Massachusetts Institute of Technology, Cambridge, Mass.

[21] Appl. No.: 30,455

[22] Filed: Apr. 16, 1979

[51] Int. Cl.³ .................. A61B 3/02; G09F 13/16
[52] U.S. Cl. ................................. 351/32; 40/582
[58] Field of Search .............. 351/32, 33, 34, 35; 40/582, 583

[56] References Cited

U.S. PATENT DOCUMENTS

| | | | |
|---|---|---|---|
| 2,385,992 | 10/1945 | Jobe | 351/32 |
| 2,463,813 | 3/1949 | Shepard | 351/32 |

OTHER PUBLICATIONS

Americant Optical Vision, "AO Project-O-Chart Projects a Variety of Subjective Eye Tests".
"Clinical Refraction", 3rd Edition, by I. M. Borish, pp. 380, 382-386.

Primary Examiner—John K. Corbin
Assistant Examiner—Rodney B. Bovernick
Attorney, Agent, or Firm—Arthur A. Smith, Jr.; Martin M. Santa

[57] ABSTRACT

An eye chart having a plurality of rows of letters where each letter is composed of a line-stroke having a plurality of adjoining black and white segments to provide an average reflectance which is the same as the reflectance of the gray background of the chart. Each row of the letters utilizes a different width line stroke (the line segments thereof are proportioned correspondingly). The sizes of the letters of each row are geometrically decreasing and are preferably in proportion to the width of the line stroke.

16 Claims, 7 Drawing Figures

EYE TESTING CHART

The Government has rights in this invention pursuant to Grant No. 5 TOl EY00090-04 from the National Institutes of Health.

This invention relates to an eye testing chart and more particularly to a chart in which the line strokes of the letters comprise alternate white and black contiguous regions on a neutral gray background having the same reflectivity as the area weighted reflectance of the black and white line strokes.

BACKGROUND OF THE INVENTION

The familiar Snellen eye testing chart uses large black, serifed letters on a white background and is the universal standard by which visual resolution is compared. A disadvantage of the Snellen chart is the fact that defocused letters can still be partially recognized by their blur patterns; much time is thus wasted as the patient whose eyes are being tested attempts to guess the letter. The design of the Snellen chart is further complicated by the fact that each letter has a different degree of recognizability.

Analysis of the spatial frequency content of the Snellen letters reveals that they contain both high and low spatial frequencies in generous measure. The blurring of the letters is attributable to lack of response to the patient's eye to the higher frequency components in the letters. However, the patient is still capable of responding to the lower frequency components by correctly identifying the blur pattern.

It is therefore an object of this invention to provide letters to be used in conjunction with an eye testing chart in which the low spatial frequencies of the letters have been minimized.

The letters used in conventional eye testing charts are discussed at length in pages 380-385 of the book, "Clinical Refraction", 3rd Edition, I. M. Borish, Professional Press, Inc., Chicago, Illinois. It is seen from this reference that the primary consideration in the prior art was the selection of groups of letters having nearly equal difficulty of recognition. Reference is made therein to an article by Walker, J. P. S., Oph. (1942): Test Type, B. J. *Oph.*, 25:555. Page 385 of the reference book shows Walker's letters to be comprised of letters formed by a 5×5 checkerboard matrix, the letter strokes so formed being either completely white or black with the opposite color of approximately the same area filling the voids of the letter to provide a square black letter with a gray background.

It is an object of this invention to provide a letter chart where the letters of a given size are of substantially equal recognizability so that the choice of a letter on a line of letters of a desired difficulty of recognition need not be restricted as in the prior art to a limited group of letters. Therefore, it is a feature of this invention that the number of different charts is limited only by the number of permutations of substantially all the letters in the alphabet (except for the letters I, M, and W which represents width extremes) and if desired of numbers. Thus, the number of permutations of the letters is substantially greater than that possible with prior art charts in which the letters of a particular line are chosen to be of equal recognition difficulty.

It is therefore an object of this invention to provide letters which have substantially less distinct blur patterns and less recognizability when not in focus than those in the prior art while those same letters which are in focus are easily recognizable.

It is a further object to provide letters which shift in and out of focus more critically with changes in letter size or viewing distance than the prior art letters.

It is a further object of this invention that the letters blend into the gray background rather than becoming partially recognizable blurs when the letters are too far defocused to be recognized without guessing.

It is a further feature of this invention that in one embodiment the letters of the eye testing chart are outlined in black with the interior portions of the letter being white on a gray background having the same reflectance as the average reflectance of the black and white areas of the letter. Alternately, the letter can be outlined in white with the inner portion being black on a gray background, the reflectance being similarly determined.

It is a further feature of one embodiment of this invention that there may be interposed on the gray background of the chart between the letters a plurality of black or white dots, asterisks, or stars to provide a "noise" background which will inhibit recognition of letters of marginal visibility.

It is a further feature of this embodiment that the line stroke used to form the letters can instead be used to form a single and easily recognized figure, such as a cat, a chair, or cup, and that different width line strokes can be similarly outlined to form a plurality of such figures so that children and other illiterates can be tested.

Other advantages, features, and objects of the invention will appear from the following description taken together with the drawings in which.

DETAILED DESCRIPTION OF THE PREFERRED EMBODIMENT

Figure 1:
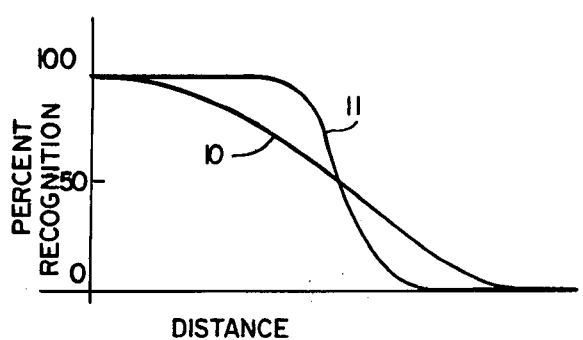
FIG. 1 depicts relative letter recognition as a function of distance for the letter chart of this invention and for the prior art chart.

FIG. 1 shows qualitatively a plot of the percent correct identification of a letter as a function of distance for a representative person being tested with different eye testing charts. The curve 10 shows that the correct determination of a letter falls off gradually with distance with the conventional type of eye testing chart. However, with the eye testing chart made in accordance with this invention, curve 11 shows that there is a sharp demarkation from near 100% correct identification of a letter to near total nonrecognizability as a function of distance. The distance at which a letter becomes unrecognizable is determined by the width of the line strokes comprising the letter. The rapid drop off of recognition as a function of distance for the eye testing chart of this invention substantially reduces the range of distances where uncertainity of recognition and guessing of letters considerably slows down the testing process.

Figure 2:
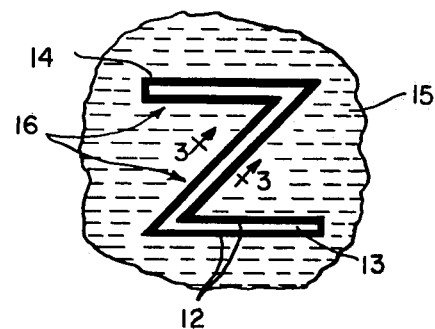
FIG. 2 is a representative letter constructed in accordance with the invention.

A typical letter constructed according to this invention which would appear on an eye chart is shown in FIG. 2. The letter Z has been chosen representative. The letter 14 is seen to be composed of line strokes 16 of equal width having an inner white region (line 13) of the same width as each of the outer black lines 12. This letter 14 appears against a gray background 15. The shade or reflectance of gray 15 is ideally equal to the weighted average of the reflectances of the contiguous black and white lines across a section 3 of the letter. Ideally, the average reflectance of the entire letter should be the same as the reflectance of the gray although this is only approximated in practice.

The letter 14 of FIG. 2 when observed within the recognition distance of the viewer will appear recognizable as the letter being depicted. However, as the distance between the observer and the letter is increased, there will be a short incremental distance over which the letter will cease to be recognizable and will disappear by blending into the gray background 15.

It should be recognized that although the terminology black and white have been used to characterize the line segments the black need not have 100% absorptance and the white may not have 100% reflectance; nonetheless, the reflectance averaged across a line stroke should still be equal to the reflectance of the background gray area.

Figure 3:
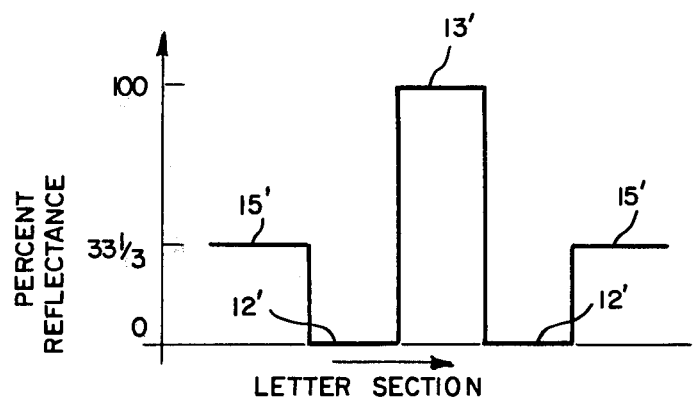
FIG. 3 is a plot of reflectance across a section of a line stroke of the letter of FIG. 2.

The reflectance of the letter 14 of FIG. 2 through the section 3 is shown in graphical form in FIG. 3. The white portion 13 of the line stroke 16 is assumed to have 100% reflectance whereas each black portion 12 is assumed to have 0% reflectance. The gray region 15 has a reflectance of 33⅓% of that of the white portion. The reflectance of each portion of the line stroke and the gray background is shown in FIG. 3 with the primed numbers corresponding to their respective portions of the character and background of FIG. 2. The average of the 100% reflectance of the white line 13 of the line stroke and the 0% reflectance of the two black lines 12 of the line stroke (all lines of equal width) have an average reflection of 33⅓% which is equal to the 33⅓% reflectance of the gray background 15 of the regions surrounding the line stroke (and the letter). Therefore, when the letter is at a greater distance from the observer than that at which the observer is capable of resolving the line stroke segments 12 and 13, the letter presents a gray appearance substantially identical to that of the gray background and therefore blends into the background.

It is of course apparent that if the reflectance of the white portion is less than 100%, for example 90%; and reflectance from the black portion is 10% than the gray background should have a different reflectance of 36⅔%, since the average reflectance over the line stroke is 36⅔%.

Figure 4:
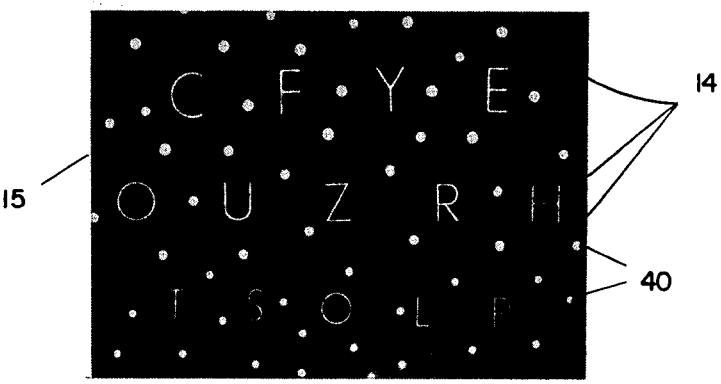
FIG. 4 is a letter chart comprised of letters constructed in accordance with FIG. 2.

FIG. 4 shows an eye testing chart in which letters such as that just described are used. The average reflectance from each letter 40 is the same as the reflectance from the gray area 15 surrounding the letter. As the letters become smaller in size, the widths of the black and white lines constituting the letter also decrease but it is not necessary that the relationship be one of exact proportionality. The visibility of a letter is determined primarily by the width of the black and white lines constituting the line stroke of the letter.

Although it is preferred to have line strokes with equal width white and black line segments, letters having unequal white and black segment widths (as in FIG. 5) also give good results. Where these segments are of unequal width, the preferred reflectance of the gray area is determined by calculating the area-weighted reflectance of the line stroke by multiplying the reflectance of each line segment by the width of the line segment, adding these calculated values, and dividing by the total width of the line stroke composed of these line segments.

The line stroke has been described as symmetrical about the center of the line stroke. It is believed that this construction of the line stroke is to be preferred especially where the letter has portions of the gray background either totally or partially enclosed by the line strokes comprising the letter, as for example in the letters A, O, or C. If the segments of the line strokes are not symmetrical about the center of the line stroke, the interior of the closed or partially closed letters will appear either darker or much lighter than the surrounding region (the Mach Band effect). It is therefore anticipated that an eye testing chart having letters with enclosed or partially enclosed letters on the gray background will best utilize a line stroke which is symmetrical about the center line of the stroke and this construction will be followed with respect to the other letters on the chart not having enclosed areas for the sake of symmetry and uniformity of presentation. However, it should be recognized that if a chart having letters which do not have substantially enclosed gray areas is used, then the desirability of symmetrical construction of line stroke is not as critical and an asymmetrical line stroke could perhaps be used.

The gray background referred to previously in the specification is preferably what is termed as neutral gray. A neutral gray is one in which reflects the same function of the incident light irrespective of the spectral energy distribution of the light source in which the chart is being viewed.

Figure 5:
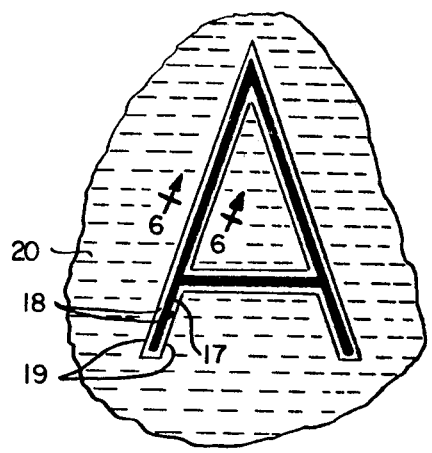
FIG. 5 is a representative letter of another embodiment of this invention.
Figure 6:
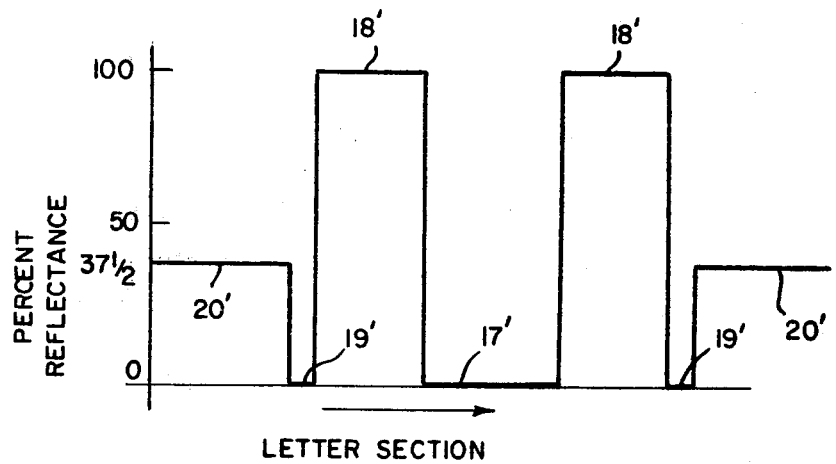
FIG. 6 is a plot of reflectance across a section of a line stroke of the letter of FIG. 5.

Another embodiment of the invention is shown in FIG. 5 where a different construction of a letter from that of FIG. 2 has been shown for purposes of illustration. In this embodiment of the invention each line segment of the letter has a total of five alternate white and black lines of unequal width. This letter also differs from that shown in FIG. 2 by having the central portion of the line stroke with a black segment instead of a white segment. The same reflectivity considerations apply to the letter shown in FIG. 5 as were discussed previously for FIG. 2. Namely, the reflectance from the white area 18 of the letter when averaged with the reflectance from the black areas 17, 19 of the letter over the width of the line stroke 20 of the letter should have the same reflectance as the gray background 21 surrounding and within the letter. The reflectance from the white and black areas of the line stroke 20 through the cross-section 6 is shown in FIG. 6 where the width 17' of the inner black line segment 17 is to be wider than the width 18' of the adjacent white line segments 18 of the line stroke 20. The outermost black line segments 19 of the line strokes each have a width 19'. If it is assumed that the width of the white lines 18 are 80% of the width of the black line 17 and that the reflectance from the white area is 100% and the reflectance from the black area is 0%, and if it is further assumed that the width 19' of the outermost black line 19 is 10% of the width of the black line 17, the reflectance of the gray background region 53 must be approximately 34% in order that the average reflectance from the letter be equal to the background reflectance. Although it has been assumed that the outermost line segment has a width 19' which is 10% of the width of the innermost line segment, the 10% width of line segment 19 is merely illustrative and the width should be that value which provides the best overall performance of the letter. Balancing of the letter reflectance with the gray background appears to affect performance more than the ratio of the line widths within the limits which have been tested. Too great a difference in the line widths as in a three line segment line stroke causes the wider line to dominate before the letter blends into the background. It has been found that a letter composed of five line segments appears to more completely blend into the surrounding gray area because of the presence of the outermost lines 19 than without their presence as in the three line segment of FIG. 2.

Figure 7:
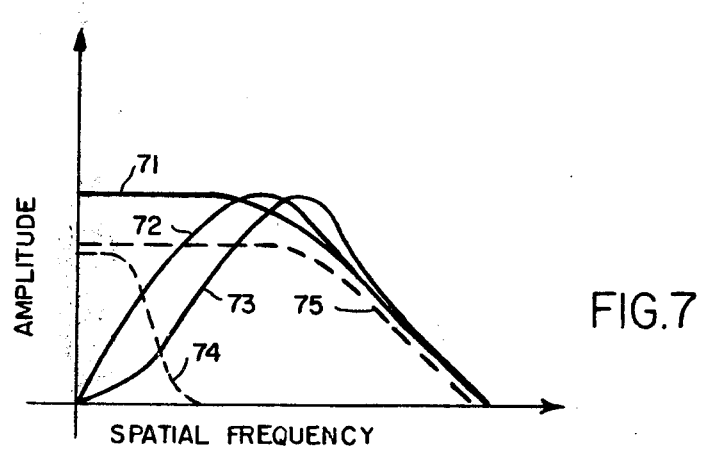
FIG. 7 is a plot of frequency responses of the eye and frequency content of letters of the prior art and of the invention.

FIG. 7 postulates curves of the average amplitude of the frequency spectrum of a letter using different types of letter strokes and also presents curves of spectral responses of the eye. Curve 71 shows the frequency distribution obtained from a conventional representative letter where the letter stroke is a single black or white line on a white or black background, respectively. This frequency distribution is a sin x/x Fourier frequency spectrum but curve 71 shows only those frequency components extending out to the first minimum. A corresponding letter using the line stroke as shown in FIG. 2 having three line segments per line stroke as a frequency spectrum shown by curve 72. It will be noted that the low frequency components of this waveform are substantially less than those of the solid line of the conventional letter. Curve 73 shows the frequency components of the same letter using five line segments per line stroke following the representation of FIG. 5. The low frequency components of the letter become progressively smaller in amplitude as the number of line segments per line stroke increases.

Curve 74 of FIG. 7 depicts the frequency response of an eye which is badly focused. It is noticed that the eye is primarily sensitive to very low spatial frequencies and hardly at all to the higher spatial frequencies. Curve 75 shows a spatial frequency response for a sharply focused eye, and it is observed that the eye is responsive out to much higher frequencies than the badly focused eye. The response of the badly focused eye is almost entirely provided by the lo frequencies. Therefore, the badly focused eye will be almost nonresponsive to a letter having the spatial frequency characteristics of curve 73, with a slightly greater response to that of curve 72, and with a much greater response from the conventional letter of curve 71. The highly focused eye provides substantial response at all spatial frequencies.

In order to test people of different acuities of vision, the chart should have letters of different widths of line strokes and preferably of proportional letter sizes although letter size is of secondary consideration. For a given width of the line stroke, the height of the letter is not critical but preferably could be substantially the same as encountered in conventional typography. For example, Futura Inline type has been used successfully in one embodiment of this invention. Serifed letters are preferably to be avoided.

Although the invention has been described in terms of a plurality of letters of different line stroke width and size for use as an eye testing chart, it will be recognized that line drawings in which the line strokes are of different widths and are such as those utilized in the formation of the letters of this invention may also be used to form line drawings of different animals and other objects recognizable by children or illiterates who are not knowledgable of the letters of the alphabet.

The letter chart of this invention shown in FIG. 4 has a galaxy of randomly placed white dots 40 on the gray background, each having a diameter roughly equal to the stroke width of the letter 14 near which it is located. Approximately three to five such dots per letter are found to be effective. This refinement greatly inhibits the recognition of letters of marginal visibility. This is evidently due to the solid white dots having appreciable low-spatial-frequency content which causes them to retain their visibility when defocused more than do the letters, thus functioning as an "effective" noise background. However, when the letters are in focus, the background of dots is easily ignored. It has been found that with the addition of the dots, photographic reproductions of charts which were unsatisfactory because of an uneven gray scale of the photo-reproduction functioned almost as well as the original having an even gray scale. It will understood that the dots may be black, as well as white, and that they may assume other shapes such as stars or astericks. It is preferred that the dot be of the same shade as the inner-line of the stroke. The diameter of the "noise" dots is not critical but the choice of the diameter approximately equal to the line stroke of the character near which it is located appears to function very satisfactorily.

The invention has been described in terms of letters of the alphabet, numerals, and line drawings all of which may be characterized by the terminology "line-figures".

It is evident that those skilled in the art, once given the benefit of the foregoing disclosure, may make numerous other uses and modifications of, and departures from the specific embodiments described herein without departing from the inventive concepts. Consequently, the invention is to be construed as embracing each and every novel combination of features present in, or possessed by, the apparatus and techniques herein disclosed and limited solely by the scope and spirit of the appended claims. For example, the "noise" dots may be applied to conventional eye testing charts by providing black "dots" on the background where the size of the dots is sufficiently large to inhibit the recognition of the out-of-focus blur pattern.

What is claimed is:

1. A line figure comprising at least one line stroke, each line stroke comprising line segments, with at least two of said line segments of different reflectances, each said line stroke being on a gray background, said gray background having the same average reflectance as the average reflectance of the line stroke, said line figure being composed of said line strokes whereby said figure blends into the gray background when said figure is at a distance beyond the resolution capability of a viewer.

2. The line figures of claim 1 comprising
   a plurality of line strokes, each line stroke comprising a plurality of contiguous black and white lines,
   the average of the reflectance of the line strokes being substantially the same as the reflectance from said gray background.

3. The line figure of claim 1 wherein said line stroke comprises at least three contiguous black and white lines, the average reflectance of said lines being substantially the same as the reflectance from said gray background.

4. The line figure of claim 1 wherein said line segments are of substantially equal width.

5. The line figure of claim 1 wherein said line stroke comprises at least five contiguous black and white line segments, the average reflectance of each of said line strokes being substantially the same as the reflectance of said gray background,
the width of the outermost line segments of said line stroke being substantially narrower than the width of the innermost line segment of said stroke.

6. The line figure of claim 1 comprising in addition,
a plurality of black or white regions on the gray background whose width is of the order of the width of the line stroke in proximity to said regions.

7. An eye testing chart comprising
a plurality of letters on a gray background,
said letters being arranged to provide a plurality of rows, the letters in a row being of the same height and formed of line strokes of the same width, each line stroke comprising a plurality of contiguous line segments, each line segment being of substantially different reflectivity from its adjacent line segment,
each row having letters of a different width line stroke and a proportionately different height from the other rows,
the line strokes in each row having the same average reflectivity as the line strokes in every other row,
said gray background having substantially the said value of reflectivity as the average reflectivity of said line strokes,
whereby said letters blend into the grey background when said letters are at a distance beyound the resolution capability of a viewer.

8. The chart of claim 7 wherein said contiguous line segments are a black line segment and a white line segment.

9. The chart of claim 8 wherein the number of line segments is an odd number and the innermost line segment is symmetrical with respect to the center of the line stroke.

10. The chart of claim 9 wherein the number of line segments is three.

11. The chart of claim 10 wherein the line segments are substantially of equal width.

12. The chart of claim 9 wherein the number of line segments is five and the width of the outermost line segments are an order smaller than magnitude of the width of the innermost line segment.

13. The chart of claim 8 comprising in addition
a plurality of regions of substantially different reflectivity from said gray background disposed on said background,
the area of said regions being proportional to the width of the line strokes of the letters to which the dots are proximate.

14. The chart of claim 13 wherein said regions are dots having a diameter substantially equal to the width of the line strokes to which the dots are proximate.

15. An eye testing chart comprising,
a plurality of figures on a gray background,
at least one of each of said figures being formed of a different line stroke width from every other figure,
each line stroke comprising a sequence of contiguous line segments wherein each line segment has a substantially different reflectivity from its adjacent line segment, reflectivity, the width of each line segments of a line stroke being directly proportional to the width of the line stroke in which it is contained, each line stroke thereby having the same average reflectivity,
said gray background having substantially the same value of reflectivity as said line stroke average reflectivity,
whereby said Figures blend into the grey background when said Figures are at a distance beyond the resolution capability of a viewer.

16. The chart of claim 7 wherein
each row of letters has a different resolution from each other row of letters,
and further comprising a plurality of dots randomly interposed between said letters, the size of each dot being proportional to the size of the letters to which the dot is proximate.

* * * * *